United States Patent [19]
Snell et al.

[11] Patent Number: 5,811,272
[45] Date of Patent: Sep. 22, 1998

[54] METHOD FOR CONTROLLING MOLECULAR WEIGHT OF POLYHYDROXYALKANOATES

[75] Inventors: Kristi D. Snell, Belmont, Mass.; Scott A. Hogan, Troy, Mich.; Sang Jun Sim, Seoul, Rep. of Korea; Anthony J. Sinskey; Chokyun Rha, both of Boston, Mass.

[73] Assignee: Massachusetts Institute of Technology, Cambridge, Mass.

[21] Appl. No.: 687,806

[22] Filed: Jul. 26, 1996

[51] Int. Cl.⁶ .................. C12P 7/62; C12P 7/52; C12N 1/00; C12N 5/02
[52] U.S. Cl. .................. 435/135; 435/141; 435/243; 435/375
[58] Field of Search .................. 435/375, 135, 435/141, 69.1, 70.1, 71.1

[56] References Cited

U.S. PATENT DOCUMENTS

| | | | |
|---|---|---|---|
| 4,477,654 | 10/1984 | Holmes et al. | 528/361 |
| 5,245,023 | 9/1993 | Peoples et al. | 536/23.2 |

FOREIGN PATENT DOCUMENTS

| | | |
|---|---|---|
| 4417 169 A1 | 11/1995 | Germany . |
| WO 89/00202 | 1/1989 | WIPO . |
| WO 91/00917 | 1/1991 | WIPO . |
| WO 95/21257 | 8/1995 | WIPO . |
| WO 95/21260 | 8/1995 | WIPO . |
| WO 96/05316 | 2/1996 | WIPO . |

OTHER PUBLICATIONS

Anderson and Dawes, Occurrence, Metabolism, Metabolic Role, and Industrial Uses of Bacterial Polyhydroxyalkanoates, *Microbiological Reviews,* 54(4), 450–472 (1990).

Berg, D.E., et al., "The Prokaryotic Transposable Element Tn5," *Biotechnology,* 1, 417–135 (1983).

Berndt and Schlegel, "Kinetics and Properties of β–Ketothiolase from *Clostridium pasteurianum,*" to *Arch. Microbiol.,* 103, 21–30 (1975).

deSmet, et al., "Characterization of Intracellular Inclusions Formed by *Pseudomonas olevorans* During Growth on Octane," *J. Bacteriol.,* 154, 870–878 (1983).

Ditta, et al., "Broad Host Range DNA Cloning System for Gram–Negative Bacteria: Construction of a Gene Bank of *Rhizobium melioti,*" *Proc. Natl. Acad. Sci. USA,* 77, 7347–7351 (1980).

Fukui et al., "Enzymatic Synthesis of Poly–β–Hydroxybutyrate in *Zoogloea ramigera,*" *Microbiol.* 1976, 110, 149–156.

Fukui, et al., "Purification and Characterization of NADP–linked acctoacetyl–CoA Reductase from *Zoogloea ramigera* 1–16–M," *Biochem. Biophys. Acta,* 917, 365–371 (1987).

Gerngross et al., "Overexpression and Purification of the Soluble Polyhydroxyalkanoate Synthase from *Alcaligense eutrophus:* Evidence for a Required Posttranslational Modification for Catalytic Activity," *Biochemistry,* 33, 9311–9320 (1994).

Gerngross and Martin, "Enzyme–catalyzed synthesis of Poly[(R)–(–)–3–hydroxybutyrate]: Formation of Macroscopic granules in vitro,," *Proc. Natl. Acad. Sci. USA* 92, 6279–6283 (Jul. 1995).

Gilbert, "Molecular Weight Distributions in Free–Radical Polymerizations: Their Cause and Cure" *Trends in Polymer Science* 3, 222–226 (1995).

Griebel and Merrick, "Metabolism of Poly–β–Hydroxybutyrate: Effect of Mild Alkaline Extraction on Native Poly–Hydroxybutyrate Granules," *J. Bacteriol,* 108, 782–789 (1971).

Guzman et al., "Tight Regulation, Modulation, and High–Level Expression of Vectors Containing the Arabinose $P_{BAD}$ Promoter," *J. Bacteriol.* 177, 4121–4130, 1995.

Hahn et al., "Communication to the Editor: Optimization of Microbial Poly(3–hydroxybutyrate) Recovery Using Dispersions of Sodium Hypochlorite Solution and Chloroform," *Biotechnology and Bioengineering,* 44, 256–261 (1994).

Haywood et al., "The Importance of PHB–synthase Substrate Specificity in Polyhydroxyalkanoate Synthesis of *Alcaligenes eutrophus,*" *FEMS Microbiology Letters,* 57, 1–6 (1989).

Huang and Reusch, "Genetic Competence in Escherichia coli Requires Poly–β–Hydroxybutyrate/Calium Polyphosphate Membrane Complexes and Certain Divalent Cations," *J. Bacteriol.* 177(2), 486–490 (1995).

(List continued on next page.)

Primary Examiner—Terry A. McKelvey
Attorney, Agent, or Firm—Arnall Golden & Gregory, LLP

[57] ABSTRACT

A method has been developed for control of molecular weight and molecular weight dispersity during production of polyhydroxyalkanoates in genetically engineered organism by control of the level and time of expression of one or more PHA synthases in the organisms. The method was demonstrated by constructing a synthetic operon for PHA production in *E. coli* in which the level of PHA synthase activity could be tightly controlled by placement of the synthase behind an inducible promoter. Modulation of the total level of PHA synthase activity in the host cell by varying the concentration of the inducer, isopropyl β-D-thiogalactoside (IPTG), was found to effect the molecular weight of the polymer produced in the cell. Specifically, high concentrations of synthase activity were found to yield polymers of (1983). low molecular weight while low concentrations of synthase activity yielded polymers of higher molecular weight. Polymer molecular weight dispersity is also proportional to the amount of synthase activity, with less dispersity in polyhydroxyalkanoate compositions produced in expression systems with an initial burst of synthase activity, and higher levels of molecular weight dispersity in polyhydroxyalkanoate compositions produced in expression systems with the levels of synthase activity varied during synthesis of the polyhydroxyalkanoate.

6 Claims, 8 Drawing Sheets

OTHER PUBLICATIONS

Huisman, et al., "Metabolism of Poly(3–hydroxyalkanoates) (PHAs) by *Pseudomonas oleovorans,*" *J. Biol. Chem.* 266(4), 2191–2198 (1991).

Hustede, et al., "Characterization of the Polyhydroxyalkanoate Synthease Gene Locus of *Rhodobacter sphaeroides,*" *Biotechnol. Lett.* 15(7), 709–714 (1993).

Kawaguchi and Doi, "Kinetics nd Mechanism of Synthesis and Degradation of Poly(3–hydroxybutyrate) in *Alcaligenses eutrophus,*" *Macromolecules* 25, 2324–2329 (1992).

Kidwell et al., "Regulated Expression of the *Alcaligenese eutrophus pha* Biosynthesis Genes in Escherichia coli", *Applied and Environmental Microbiology* 61(4), 1391–1398 (1995).

Kim et al., "Production of Poly–β–Hydroxybutyrate by Fed–Batch Culture of Recombinant Escherichia coli," *Biotechnology Letters,* 14(9), 811–818 (1992).

Klechner, N., et al., "Genetic Engineering in Vivo Using Translocatable Drug–resistance Elements," *J. Mol. Biol.,* 116, 125–159 (1977).

Koizumi, et al., "Molecular Weight of Poly(3–hyroxybutyrate) During Biological Polymerization in Alcaligenes eutrophus," *Chemical Abstracts,* 124:50315f (1996).

Law and Slepecky, "Assay of Poly–β–Hydroxybutyric Acid," *J. Bacteriol.* 82, 33–36 (1961).

Lee, et al., "Construction of Plasmids, Estimation of Plasmid Stability, and Use of Stable Plasmids for the Production of Poly(3–Hydroxybutyric acid) by Recombinant Escherichia coli," *Journal of Biotechnology* 32, 203–211 (1994).

Lee, S. Y., "Bacterial Polyhydroxyalkanoates," Biotechnology and Bioengineering 49, 1–14, (1996).

Lee, et al., "Production of Poly(β–Hydroxybutyric Acid) by Recombinant Escherichia coli*ª*", *Annals of the New Your Academy of Sciences,* 721, 43–53 (1994).

Liebergesell, et al., "Cloning and Nucleotide Sequences of Genes Relevant for Biosynthesis of Poly(3–Hydroxybutric acid) in *Chromatium vinosum* strain D," *Eur. J. Biochem.* 209, 135–150 (1992).

Liebergesell, et al., "Cloning and Molecular Analysis of the Poly(3–Hydroxybutyric Acid) Biosynthetic Genes of *Thiocystis violacea,*" *Appl. Microbiol. Biotechnol.,* 38, 493–501 (1993).

Nawrath et al., "Targeting of the Polyhydroxybutyrate biosynthetic pathway to the Plastids of *Arabidopsis thaliana* results in high levels of polymer accumulation," *Proc. Natl. Acad. Sci USA* 91, 12760–12764, 1994.

Nishimura et al., "Purification and Properties of β–Ketothiolase from *Zoogloea ramigera,*" *Arch. Microbiol.* 1978, 116, 21–27.

Oeding and Schlegel, β–Ketothiolase from *Hydrogenomonas eutropha* H16 and its Significance in the Regulation of Poly–β–hydroxybutyrate Metabolism, *Biochm. J.,* 134, 239–248 (1973).

Peoples and Sinskey, "Poly–β–hydroxybutyrate Biosynthesis in *Alicaligenes eutrophus* H16," *J. Biol. Chem.* 1989, 264, 15293–15297.

Peoples and Sinskey, "Poly–β–Hydroxybutyrate (PHB) Biosynthesis in *Alcaligense eutrophus* H16," *J. Biol. Chem.* 1989, 264, 15298–15303.

Peoples, et al., "Biosynthetic Thiolase from*Zoogloea ramigera,*" *J. Biol. Chem.,* 262, 97–102 (1987).

Pieper, et al., "Identification Cloning and Sequence Analysis of the Poly(3–Hydroxyalkanoic Acid) Synthase Gene of the Gram–Positive bacterium *Rhodococcus ruber,*" *FEMS Microbiol. Lett.,* 96, 73–80 (1992).

Ploux, et al., "the NADPH–linked Acetoacetyl–CoA–Reductase from *Zoogloea ramigera:* Characterization and Mechanistic Studies of the Cloned Enzyme Over–Produced in Escherichia coli," *Eur. J. Biochem.* 174, 177–182 (1988).

Poirier et al., "Production of Polyhydroxyalkanoates, a Family of Biodegradable Plastics and Elastomers, in Bacteria and Plants," *Bio/Technology* 13, 142–150 (1995).

Rhie and Dennis, "Role of fadR and atoC(Con) Mutations in Poly(3–Hydroxybutyrate–Co–3–Hydroxyvalerate) Synthesis in Recombinant ph Escherichia coli," *Applied and Environmental Microbiology,* 1995, 61, 2487–2492.

Saito, et al., "An NADP–Linked Acetoacetyl CoA Reductase from *Zoogloea ramigera,*" *Arch. Microbiol.,* 114, 211–217 (1977).

Schembri, et al., "Cloning and Analysis of the Polyhydroxyalkanoic acid Synthase Gene from an Acinetobacter sp.: Evidence that the Gene is Both Plasmid and Chromosomally Located," *FEMS Microbiol. Lett.* 118, 145–152 (1994).

Schlegel, et al., "The Isolation of Mutants Not Accumulating Poly–β–Hydroxybutyric Acid," *Arch. Microbiol.,* 71, 283–294 (1970).

Schubert et al., "Cloning of the *Alcaligense eutrophus* Genes for Synthesis of Poly–β–Hydroxybutyric Acid (PHB) and Synthesis of PHB in Escherichia coli," *J. Bacteriol.* 1988, 170, 5837–5847.

Senior and Dawes, "The Regulation of Poly–β–hydroxybutyrate Metabolism in *Azotobacter beijerinckii,*" *Biochem. J,* 134, 225–238 (1973).

Sim, et al., "PHA Synthase Activity Controls the Molecular Weight and Polydispersity of Polyhydroxybutyrate in Vivo," 126: 86943q (1997).

Simon, R., et al., "A Broad Host Range Mobilization System for In Vivo Genetic Engineering: Transposon Mutagenesis in Gram Negative Bacteria," *Biotech.,* 1 (9), 784–791 (1983).

Simon, "High Frequency Mobilization of Gram–Negative Bacterial Replicons by the In Vitro Costructed Tn5–Mob Transpoon," *Mol. Gen.,* 196, 413–420 (1984).

Slater et al., "Cloning and Expression in Escherichia coli of the *Alcaligenes eutrophilus* H16 Poly–B–Hydroxybutyrate Biosynthetic Pathway," *J. Bacteriol.* 1988, 170, 4431–4436.

Spratt, S.K., et al., "Cloning, Mapping, and Expression of Genes Involved in the Fatty Acid–Degradation Multienzyme Comlex of Escherichia coli," *J. Bacteriol.,* 158 (2), 535–547 (1984).

Timm, et al., "Cloning and Molecular Analysis of the Poly(3–Hydroxyalkanoic acid) Gene Locus of *Pseudomonas aeruginosa* PAO1," *Eur. J. Biochem,* 209, 15–30 (1992).

Tolentino et al, "A pH–Regulated Promoter for the Expression of Recombinant Proteins in Excherichia coli," *Biotechnology Letters,* 14(3),157–162, (1992).

Tomita, et al., "Bacterial Metabolism of Poly–β–Hydroxybutyrate," *Biochemistry of Metabolic Processes,* 353–367, D. Lennon, et al. editors (Elsevier, Holland, 1983).

Ueda, et al., "Molecular Analysis of the Poly(3–Hydroxyalkanoate) Synthase Gene fro a Methylotrophic Bacterium, *Paracoccus denitrifans,*" *Journal of Bacteriology* 178(3), 774–779 (1996).

University of Groningen, The Netherlands, 1991, and Huisman, et al., "Synthesis of Poly(3–Hydroxyalkanoates) by Mutant and Recombinant Pseudomonas Strains," *Appl. Microbiol. Biotechnol.* 38:1–5 (1992).

Valentin, et al., "Cloning and Characterization of the *Methylobacterium extorquens* Polyhydroxyalkanoic–acid–syn thase Structural Gene," *Appl. Microbiol. Biotechnol.* 39, 309–317 (1993).

Van Dyk et al., "Synergistic Induction of the Heat Shock Response in Echerichia coli by Simultaneous Treatment with Chemical Inducers," *J. Bacteriol.* 177, 6001–6004 (1995).

Young, R.A., et al., "Efficient Isolation of Genes by Using Antibody Probes," *Proc. Natl. Acad. Sci. USA,* 80, 1194–1195 (1983).

Young and Davis, "Yeast RNA Polymerase II Genes: Isolation with Antibody Probes," *Science,* 222: 778–782

METHOD FOR CONTROLLING MOLECULAR WEIGHT OF POLYHYDROXYALKANOATES

The United States government has certain rights in this invention by virtue of National Institutes of Health grant NIH-1-RO1-GM49171-01A1 to JoAnne Stubbe, A. J. Sinskey, and S. Masamune.

BACKGROUND OF THE INVENTION

This invention relates to controlling the molecular weight and distribution of polyhydroxyalkanoates produced in vivo in a host cell by genetically engineering the amount of polyhydroxyalkanoate polymerase which is expressed in the host cell.

Polyhydroxyalkanoates (PHAs) are a class of polyesters that are produced by many organisms as an intracellular energy reserve during nutrient deprivation (Anderson and Dawes, *Microbiological Reviews*, 1990, 54, 450–472.; Poirier et al., *Bio/Technoloy* 1995, 13, 142–150.). Since PHAs are naturally biodegradable, they are considered an attractive alternative to conventional plastics in terms of reducing solid waste. *Alcaligenes eutrophus* is an example of an organism that produces abundant granules of the polyester during nutrient limiting conditions. The PHA biosynthetic pathway in *A. eutrophus* consists of three enzymes, a thiolase, a reductase, and a synthase. Two acetyl-CoA units are condensed by β-ketothiolase to form acetoacetyl-CoA, which is stereospecifically reduced by an NADPH dependent reductase to form 3-D-hydroxybutyryl-CoA (HBCoA). PHA synthase catalyzes the polymerization of HBCoA monomer units to form polymer.

biology 1995, 61, 1391–1398), however little effort has been made to characterize the size of the polymer produced or to develop methods to control polymer molecular weight. As reviewed by Gilbert, "Molecular Weight Distributions in Free-Radical Polymerizations: Their Cause and Cure" *Trends in Polymer Science* 1995, 3, 222–226, the average molecular weight and the molecular weight distribution are some of the most important determinants of the properties of a polymer.

Gerngross and Martin, *Proc. Natl. Acad. Sci. USA* 92:6279–6283 (Jul. 1995), describe a method for increasing the molecular mass of poly[(R)-(-)-3-hydroxybutyrate] (PHB) granules by exposing purified PHA synthase to (R)-3-hydroxybutyryl coenzyme A, and determined that the molecular mass of the polymer is dependent on the initial PHA synthase concentration in a cell free, in vitro system wherein specific substrate is added. While this is an interesting research observation, it provides little basis on which commercial synthesis of polymer of defined molecular weight can be produced in a bacterial system where many other enzymes and substrates are present. The substrate needed for in vitro polymerization, D-3-hydroxybutyrylCoA, is only commercially available as a mixture of D and L diasteriosomers. The current cost of D,L-3-hydroxybutyrylCoA from Sigma Chemical Company, St. Louis, Mo., is $187.55 for 25 milligrams of material.

Huisman, in his Ph.D. thesis entitled "Synthesis of poly (3-hydroxyalkanoates) by mutant and recombinant strains of *Pseudomonas putida*" submitted to the University of Groningen, The Netherlands, 1991, and Huisman, et al., *Appl. Microbiol. Biotechnol.* 38:1–5 (1992), analysed the poly(3-hydroxyalkanoates) produced in mutants defective in The operon containing the PHA biosynthetic genes from *A. eutrophus* has been cloned, allowing its expression in *Escherichia coli* (Peoples and Sinskey, *J. Biol. Chem.* 1989, 264, 15298–15303; *J. Biol. Chem.* 1989, 264, 15293–15297; Slater et al., *J. Bacteriol.* 1988, 170, 4431–4436; Schubert et al., *J. Bacteriol.* 1988, 170, 5837–5847). Wild-type *E. coli* is itself capable of producing small amounts of a form of polyhydroxybutyrate (PHB) that is found complexed to the cell membranes (Huang and Reusch, *J. Bacteriol.* 1993, 177, 486–490), however the abundant granules found in other microorganisms such as *A. eutrophus* during nutrient limiting conditions are not present in *E. coli*. Insertion of a plasmid-borne copy of the PHA biosynthetic operon from *A. eutrophus* enables *E. coli* to produce PHB granules visible by transmission electron microscopy (Lee et al., 1994a). Considerable attention has been devoted to the fermentation of genetically engineered *E. coli* PHB producers (Lee et al., 1994a and Lee, et al., *Journal of Biotechnology* 1994, 32, 203–211; Kim et al., *Biotechnology Letters*, 1992, 14, 811–818.; Kidwell et al., *Applied and Environmental Microbiology*

PHA metabolism. Comparisons of molecular weights and quantities of polymer were made based on the substrate provided to the mutant. It was postulated that, in addition to substrate, the polymerase played a role in determining the molecular weight of the resulting polymer. Average PHA molecular weight was theorized to be inversely proportional to polymerase activity, but the exact role and its relationship to substrate availability in final product characteristics were not determined. Moreover, the studies were conducted using plasmid-based expression of PHA synthase genes from one strain, *Pseudomonas oleovarans*, in a host of a different strain, *P. putida*, a system that does not necessarily guarantee expression. No enzyme activity data was provided to support claims of expression in this heterologous system. The strain is also capable of degrading polymer. Indeed, the results suggest degradation by depolymerases, not control of synthase activity, since polymer yields decrease with decreases in molecular weight.

Although a correlation between molecular weight of the resulting polymer and concentration of PHA synthase has been suggested, many factors, including substrate availability, clearly play a role.

It is therefore an object of this invention to provide a method for controlling polymer molecular weight and molecular weight dispersity.

SUMMARY OF THE INVENTION

A method has been developed for control of molecular weight and molecular weight dispersity during production of polyhydroxyalkanoates in genetically engineered organisms by control of the level and time of expression of one or more PHA synthases in the organisms. The method was demonstrated by constructing a synthetic operon for PHA production in *E. coli* in which the level of PHA synthase activity could be tightly controlled by placement of the synthase behind an inducible promoter. Modulation of the total level of PHA synthase activity in the host cell by varying the concentration of the inducer, isopropyl β-thiogalactoside (IPTG), was found to effect the molecular weight of the polymer produced in the cell. Specifically, high concentrations of synthase activity were found to yield polymers of low molecular weight while low concentrations of synthase activity yielded polymers of higher molecular weight. Polymer molecular weight dispersity can be controlled by modulating the synthase activity during the polymer synthesis reaction. For example, low synthase activity at the beginning of the fermentation yields high molecular weight polymer of low molecular weight dispersity; increasing synthase activity during fermentation results in synthesis of lower molecular weight polymer, thereby increasing the molecular weight dispersity of the polymer produced during the fermentation. Examples demonstrate the synthesis of polymers having a range of molecular weights between $4 \times 10^6$ and $7.8 \times 10^5$, and defined molecular weight distributions (polydispersity indices from 1.02 and 2.81).

BRIEF DESCRIPTION OF THE DRAWINGS

FIGS. 6A–6C are a graph of the polydispersity index (Mw/Mn) over time (hours) of polymer isolated from strains DH5α/pAeT41 (triangles), DH5α/pSP2 with 0.4 mM IPTG induction (circles), and DH5α/pSP2 with 5 mM IPTG induction (solid circles), as calculated by gel permeation chromatography in line with light scattering.

DETAILED DESCRIPTION OF THE INVENTION

The polyhydroxyalkanoates (PHAs) detected in bacteria can be divided into two main groups, those containing short chain monomer units (3–5 carbon atoms) and those containing medium chain monomer units (6–14 carbon atoms) (Lee, S. Y. Biotechnology and Bioengineering 49, 1–14, 1996). The synthase enzymes are generally divided into three classes: Type I, such as *A. eutrophus*, that synthesize polymer with short chain monomer units; Type II, such as *Pseudomonas oleovorans*, that synthesize polymer containing medium chain monomer units; and Type III, such as *Chromatium vinosum*, that require the expression of a second gene *phaE* for synthase activity and predominantly synthesize short chain polymers. There has been a synthase found in the type III group from *T. pfennigii* that synthesizes a copolymer composed of short and medium chain length monomer units (Poirier et al., Bio/Technology 13, 142–150, 1996).

Short chain monomer units that are recognized as substrates by the short chain PHA synthases include 3, 4, and 5-hydroxyacyl CoAs [Lee, S. Y. Biotechnology and Bioengineering 49, 1–14, 1996]. In general, the presence of a thiolase and reductase is needed to make polymer in short chain production systems. For example, 3-hydroxybutrylCoA is formed from acetylCoA via 3-ketothiolase and acetoacetyl reductase. Other short chain monomer units can be formed by adding alkanoic acids or hydroxyalkanoic acids to the bacterial growth medium. Alkanoic acids, such as propionic acid, are converted to acyl CoAs, via a CoA synthase, which are subsequently converted to hydroxyacylCoA's via a thiolase and reductase (Poirier et al., Bio/Technology 13, 142–150, 1995). However, hydroxyalkanoic acids are converted to hydroxyacylCoAs by the bacteria without the need of thiolase or reductase enzymes.

Monomer units of medium chain length PHAs are derived either from alkanoic acids added to the bacterial growth medium or from the fatty acid biosynthetic and β-oxidation pathways when the bacteria are grown on simple sugars. *P. oleovorans* is an exception in that it has not been found to produce PHAs when grown on simple sugars (Poirier et al., Bio/Technology 13, 142–150, 1995). Acyl CoAs, formed from the alkanoic acid via an acyl CoA synthase, are converted to hydroxyacyl CoAs by the β-oxidation pathway (Poirier et al., Bio/Technology 13, 142–50, 1995). Thus, medium chain length polymer production systems do not need the thiolase and reductase, however, they do require the presence of β-oxidation and fatty acid biosynthetic pathway enzymes.

Molecular weight control by controlling synthase activity applies to all classes of polymers, not just PHB, as well as all classes of synthases.

PHA Synthases Many different PHA synthases are known, characterized and the encoding DNA is sequenced. These are generally derived from natural sources, but can include synthases with conservative substitutions in the amino acid sequences.

References for sequences of known synthases include: *Paracoccus denitrificans:* Ueda, et al., *Journal of Bacteriology* 1996, 178, 774–779; *A. eutrophus:* Peoples, et al., *J. Biol. Chem.* 1989, 264, 15293–15297 (Genbank accession number JO5003); *Acinetobacter* sp.: Schembri, et al., *FEMS Microbiol. Lett.* 1994, 118, 145–152; *Chromatium vinosum:* Liebergesell, et al., *Eur. J. Biochem.* 1992, 209, 135–150; *M. extorquens:* Valentin, et al., *Appl. Microbiol. Biotechnol.* 1993, 39, 309–317; *Pseudomonas aeruginosa* 1 and 2: Timm, et al. *Eur. J. Biochem,* 1992, 209, 15–30; *Pseudomonas oleovorans* 1 and 2: Huisman, *J. Biol. Chem.* 1991, 266, 2191–2198; *Rhodococcus ruber:* Pieper, et al., *FEMS Microbiol. Lett.,* 1992, 96, 73–80; *R. sphaeroides:* Hustede, et al., *Biotechnol. Lett.* 1993, 15, 709–714; *Thiocystis violacea:* Liebergesell, et al., 1993, 38, 493–501.

Thiolases and Reductases

*A. eutrophus* thiolase and reductase are described by Peoples and Sinskey, *J. Biol. Chem.,* 264, 15293–15297 (1989) and available from Genbank under the accession number JO4987.

Depolymerases

In *E. coli* it is not necessary to inactivate the depolymerase since there is no known depolymerase and degradation has not been observed. However, in other host strains where a functional depolymerase exists, it would be desirable to eliminate the depolymerase so that the polymer product does not degrade. A depolymerase can be inactivated by mutagenesis of the host strain.

Expression Vectors

The gene encoding the synthase, as well as any other enzymes such as the reductase and thiolase, can be inserted into an appropriate vector for expression in a host system. In the preferred embodiment, the vector is a plasmid expressable in a bacteria such as *Escherichia coli*. Suitable plasmids can be obtained from commercial sources including the American Type Culture Collection, Rockville, Md. Other commercial sources for expression vectors include Pharmacia Biotech Inc., Piscataway, N.J.; Clontech Laboratories, Inc., Palo Alto, Calif.; Promega, Madison, Wis.

In the preferred embodiment, expression of the synthase is under the control of an inducible promoter, as demonstrated by the following examples. Promoters that can be utilized to regulate the expression of PHA synthase in bacterial hosts include, but are not limited to, an IPTG inducible promoter such as the lac, trc, or tac promoters; a pH regulated promoter regulated by pH (Tolentino et al, Biotechnology Letters, 14, 157–162, 1992); a pH regulated promoter regulated by aerobic or anaerobic conditions (Tolentino et al.); a pH regulated promoter regulated by combining pH control with anaerobic/aerobic conditions (Tolentino et al.); an arabinose controlled promoter regulated by arabinose levels in culture media (Guzman et al., J. Bacteriol. 177, 4121–4130, 1995); repression of an arabinose controlled promoter with glucose yielding extremely low levels of synthase expression Guzman et al.); a T7 RNA polymerase promoter such as ø10 regulated by T7 RNA polymerase; the promoter regions of heat shock genes such as *dnaK, grpE,* and *lon,* that can be induced either through heat shock or other environmental stresses such as the addition of chemical inducers such as ethanol (Van Dyk et al., J. Bacteriol. 177, 6001–6004, 1995).

Expression Systems

In the preferred embodiment, the host is a bacteria which has been genetically engineered so that it secretes polymer rather than accumulating it in insoluble granules, for example, by genetically engineering the host cell with a gene that allows lysis of the cells when induced. The most preferred host is *E. coli*. Others include Gram positive bacteria such as *Corynebacterium, Pseudomonas,* eukaryotic cells, and plant hosts.

Prokaryotic, eukaryotic and plant systems can be created to produce a range of polymers possessing different molecular weights and polydispersities by placing promoters in front of the synthase gene that are inducible to different levels. Alternatively, a series of separate strains, cell lines, or plants containing constitutive promoters of different strengths could be created such that each strain, cell line, or plant produces one polymer product of the desired molecular weight and polydispersity.

In bacterial hosts, synthase activity can be further regulated by employing constituative or inducible promoters in front of synthase genes in low copy number plasmids, such as those containing the pSC101 replicon, medium copy number plasmids, such as those containing the pMB1, p15A, or ColEl replicons, high copy number plasmids, such as the pUC plasmids containing a mutated pMB1 replicon, chromosomal insertion of a single copy of the gene into a host strain, or chromosomal insertion of multiple copies of the gene into a host strain.

In plants, expression systems for generating polymers possessing different molecular weights can include the construction of a stably transformed plant containing genes encoding the reductase and thiolase, in which the synthase gene is located behind an inducible promoter, such as the soybean heat-shock promoter Gmgsp17.3. Alternatively, a series of individual stably transformed plants can be created containing genes encoding the reductase and thiolase and in which the PHA synthase gene(s) are behind constituative promoters of varying strength such that each plant has a different synthase activity and therefore produces a polymer of different molecular weight. PHA production can be targeted to the plastids of the plants by fusing a transit peptide, such as the pea chloroplast transit peptide, to the thiolase, reductase, and synthase enzymes, a strategy that has been shown to increase polymer yields in transgenic plants (Nawrath et al., Proc. Natl. Acad. Sci USA 91, 12760–12764, 1994).

Fermentation Conditions

Fermentation conditions that can be used for producing PHA's in bacteria include batch fermentation and continuous culture. Carbon sources for either fermentation can be simple sugars or alkanoic or hydroxyalkanoic acids supplemented to the culture medium depending on the type of PHA that is desired and the genetic background of the host production organism. For example, the co-polymer of 3-hydroxybutyrate and 3-hydroxyvalerate can be formed in *E. coli* by adding propionic acid to the culture medium of an *atoC fadR* mutant strain (Rhie and Dennis, Applied and Environmental Microbiology, 1995, 61, 2487–2492).

The data presented in the examples led to the identification of PHA synthase as the component responsible for controlling the molecular weight of PHA biosynthesized in genetically recombinant bacteria such as *E. coli*. Two constructs were examined, DH5α/pAeT41, containing the native *A. eutrophus* PHA biosynthetic operon, and DH5α/pSP2, containing a modified operon in which the ribosome binding site in front of the synthase has been optimized and the transcription of the PHA biosynthetic genes is under the control of an inducible promoter. The role of the synthase in determining the molecular weight of the polymer is most evident upon comparison of the fermentations of DH5α/pAeT41 and DH5α/pSP2, induced with 0.4 mM IPTG. Synthase activity, both soluble and insoluble, remains at a constant undetectable level throughout the fermentation of DH5α/pAeT41, yielding high molecular weight polymer of approximately constant size at the beginning ($4.3 \times 10^6$ Da) and end ($4.0 \times 10^6$ Da) of the fermentation. In contrast, an increase in insoluble synthase activity in DH5α/pSP2 (0.4 mM IPTG) is observed coincident with a decrease in polymer size, yielding polymer of significantly smaller size at the end of the fermentation ($1.3 \times 10^6$ Da) than at the beginning ($2.2 \times 10^6$ Da). Approximately equal levels of thiolase activity and little or no reductase activity are observed in both fermentations indicating that these enzymes are not responsible for the observed difference in molecular weight. The role of the synthase is further substantiated in the fermentation of DH5α/pSP2 induced with 5 mM IPTG in which in vivo synthase activities are further increased, yielding polymer of still lower molecular weight ($7.3 \times 10^5$ Da) at the end of the fermentation.

Although the described methodology for controlling molecular weight in vivo is illustrated with a genetically engineered strain of *E. coli* and PHB, it is not limited to *E. coli* or PHB and can be used in any organism expressing either native or genetically engineered PHA biosynthetic genes to produce any member of the class of polymers encompassed by polyhydroxyalkanoates. The control of PHA synthase activity is not limited to induction of an inducible promoter with IPTG, for any method capable of altering the in vivo concentration of PHA synthase activity is capable of controlling the molecular weight of polymer produced in the respective organism.

The present invention will be further understood by reference to the following non-limiting examples.

EXAMPLE 1

Production and Characterization of PHB Produced in *E. coli*.

Methods and Materials:

Fermentation of *E. coli* DH5α/pAeT41 was used to establish a reference from which to compare all other genetically engineered *E. coli* PHB producers. Plasmid pAeT41, described in U.S. Pat. No. 5,245,023 to Peoples, et al., contains a 5 kb genetic fragment encoding the native, unmodified PHA biosynthetic operon from *A. eutrophus* inserted into pUC18, Sequence Listing ID No. 1. pAeT41 (7.7 kb) is shown schematically as:

As with all other plasmids described in this study, plasmid pAeT41 was transformed into the *E. coli* strain DH5α for polyester production. Strains were cultured at 30° C. in a 15 L MCS-10 Bioreactor AG fermentor (MBR, Switzerland) in LB media (LB media contains per L, 10 g tryptone, 5 g yeast extract, and 10 g NaCl) supplemented with glucose (20 g/L) and ampicillin (50 mg/mL), As with all other fermentations in this study, aliquots of cells were removed for enzyme activity analysis at time points throughout the fermentation, pelleted by centrifugation, and frozen at −70° C. Samples were thawed, resuspended in M9 salts (M9 salts contain, per L, 6 g $Na_2HPO_4$, 3 g $KH_2PO_4$, 0.5 g NaCl, and 1 g $NH_4Cl$), and divided into three individual samples for the assay of synthase, thiolase, and reductase activity. Cells were isolated by centrifugation, resuspended in lysis buffer, and disrupted by sonication using an Ultrasonic Processor xL (Farmingdale, N.Y.). After lysis, samples were centrifuged at 4° C. for 15 min to isolate soluble protein fractions.

PHA synthase was assayed by monitoring coenzymeA release using 5, 5'-dithiobis(2-nitrobenzoic acid) as described by Gerngross et al. *Biochemistry,* 1994, 33, 9311–9320. Both the soluble protein fraction and the crude sonicated lysate were assayed, allowing the determination of both soluble and insoluble synthase enzyme activities. Prior to sonication, samples for the assay of PHA synthase were resuspended in 50 mM $KH_2PO_4$ (pH 7.0) containing 5 % glycerol. AcetoacetylCoA reductase was assayed by monitoring the oxidation of NADPH as described by Ploux et al., *Eur. J. Biochem.* 1988, 174, 177–182, with the exception that the acetoacetylCoA concentration was increased to 1.8 mM. Prior to sonication, samples for the assay of reductase activity were resuspended in 10 mM Tris-Cl (pH 8.0), 1 mM EDTA, 10 mM β-mercaptoethanol, 20% glycerol, and 0.2 mM phenylmethylsulfonyl fluoride. β-ketothiolase activity was assayed by measuring the rate of $NAD^+$formation as described by Nishimura et al., *Arch. Microbiol.* 1978, 116, 21–27. Prior to sonication, samples for the assay of thiolase activity were resuspended in 10 mM Tris-Cl (pH 7.3) containing 5 mM β-mercaptoethanol. The PHB content in fermentation broths was assayed as described by Law and Slepecky, *J. Bacteriol.* 1961, 82, 33–36. The glucose concentration in fermentation broths was determined using a 1050 Hewlett Packard HPLC system equipped with a model 1047A refractive index detector and a Bio-Rad Aminex HPX-87H column maintained at 40° C. Glucose was eluted with a mobile phase of 0.008N sulfuric acid at a flow rate of 0.6 mL/min.

Figure 1A:
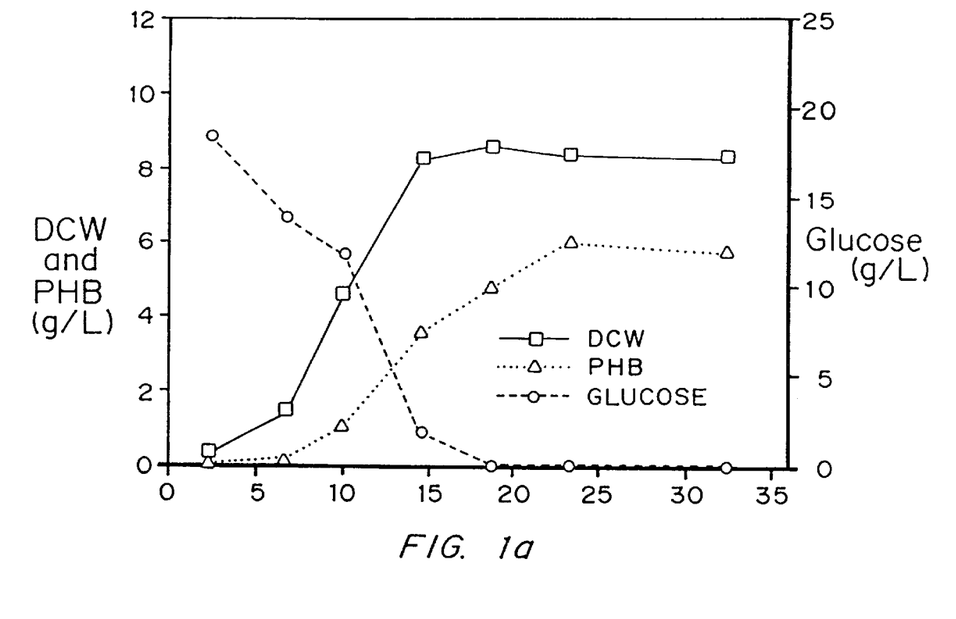
FIGS. 1A, 1B, and 1C are graphs of dry cell weight (DCW), PHB concentration (PHB), and glucose concentration during 13 L fermentations of strains DH5α/pAeT41 (FIG. 1A), DH5α/pSP2 with 0.4 mM IPTG induction (FIG. 1B), and DH5α/pSP2 with 5 mM IPTG induction (Figure 1C).
Figure 2:
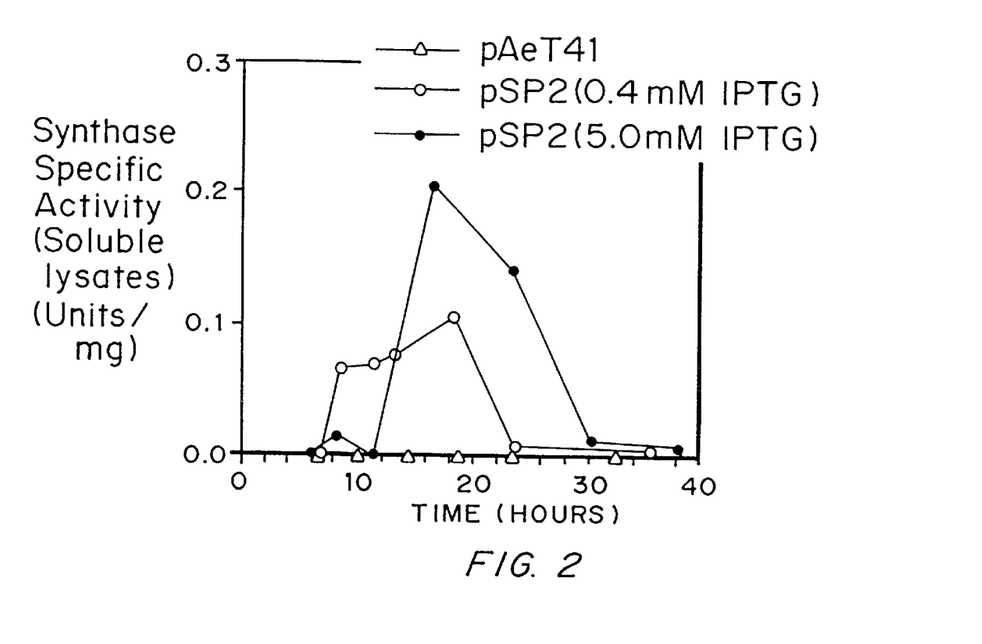
FIG. 2 is a graph of enzyme activities (specific activity, units/mg, time, hour) of the synthase in soluble lysate fractions of strains DH5α/pAeT41 (triangles), DH5α/pSP2 with 0.4 mM IPTG induction (circle), and DH5α/pSP2 with 5 mM IPTG induction (solid circle).
Figure 3A:
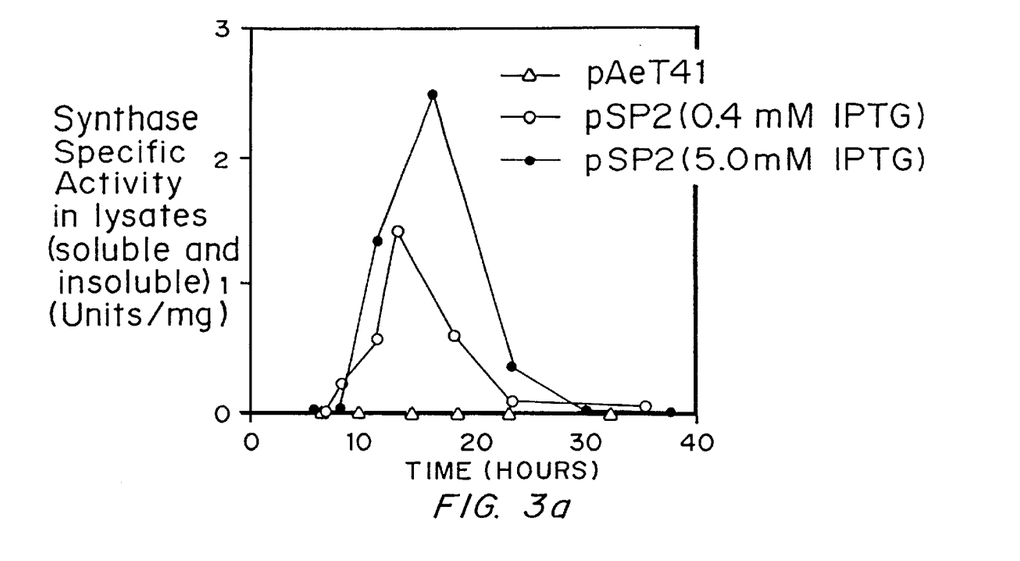
FIG. 3A is a graph of synthase activity (specific activity, units/mg over time, hour) for crude lysates of strains DH5α/pAeT41 (triangle), DH5α/pSP2 with 0.4 mM IPTG induction (circle), and DH5α/pSP2 with 5 mM IPTG induction (solid circle). The crude lysate is defined as the lysate fraction containing both soluble and insoluble enzyme fractions.
Figure 4:
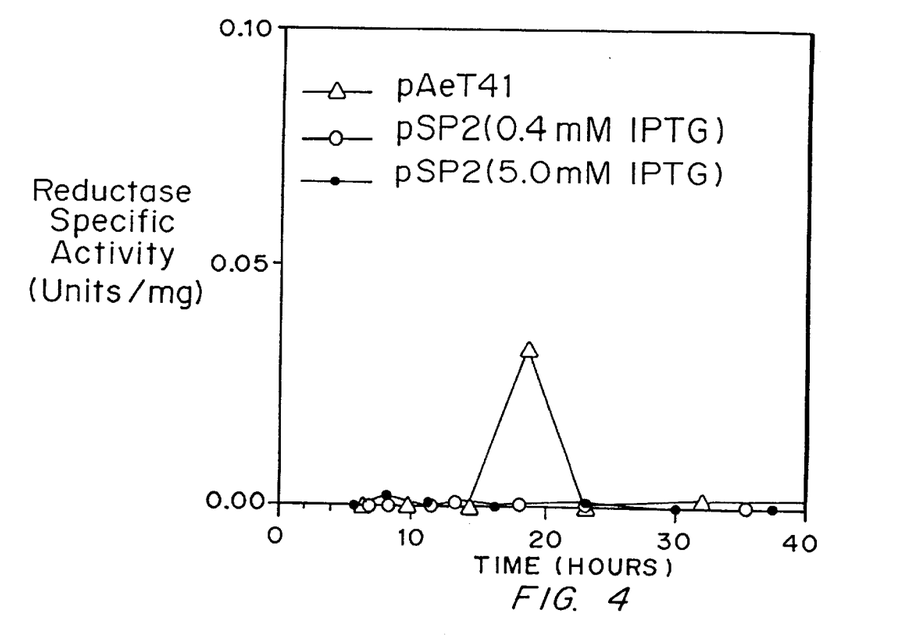
FIG. 4 is a graph of the activity of the reductase (specific activity, units/mg, over time, hours) in soluble lysate fractions of strains DH5α/pAeT41 (triangle), DH5α/pSP2 with 0.4 mM IPTG induction (circle), and DH5α/pSP2 with 5 mM IPTG induction (solid circle).
Figure 5:
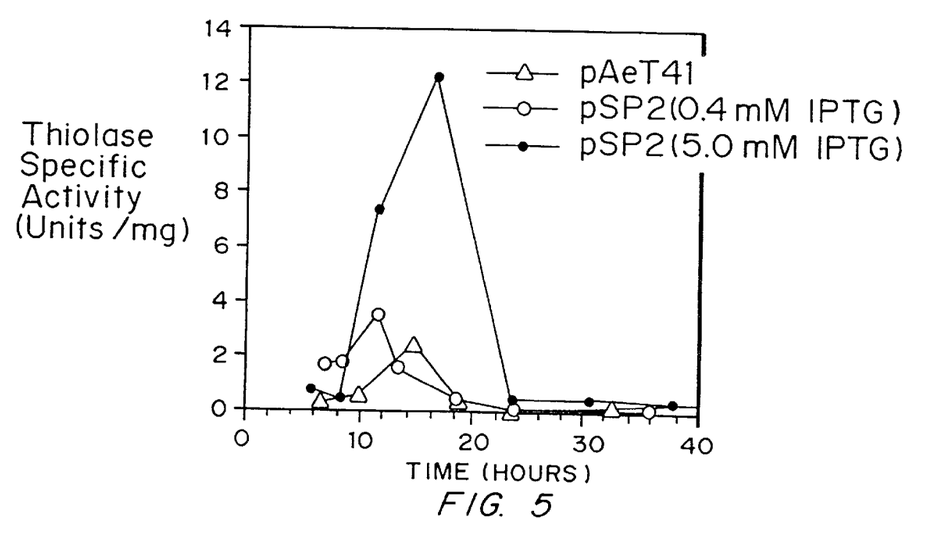
FIG. 5 is a graph of the activity of the thiolase in soluble lysate fractions of strains DH5α/pAeT41 (triangle), DH5α/pSP2 with 0.4 mM IPTG induction (circles), and DH5α/pSP2 with 5 mM IPTG induction (solid circles).

During batch fermentation of DH5α/pAeT41 (FIG. 1A), the initial 20 g/L of glucose supplied to the cells was completely consumed after 18.7 h. Dry cell weight and PHB concentration reached a maximum of 8.7 and 6.0 g/L after 18.7 and 23.3 h of fermentation, respectively. Despite localization of the *A. eutrophus* PHA biosynthetic operon on the high copy plasmid pUC18, no soluble PHA synthase activity was detected during the entire DH5α/pAeT41 fermentation (FIG. 2). The presence of polymer in cell lysates often results in localization of synthase activity in the insoluble portion of the lysate (Fukui et al., *Microbiol.* 1976, 110, 149–156.; Haywood et al., *FEMS Microbiology Letters,* 1989, 57, 1–6). An additional assay was thus performed for all fermentation samples by measuring the combined soluble and insoluble fractions in the crude lysate prior to centrifugation. DH5α/pAeT41 lysates assayed in this way still contained no detectable synthase activity (FIG. 3A). Maximum reductase activity of 0.033 U/mg was observed at 18.7 h (FIG. 4) while assays for thiolase activity yielded a maximum of 2.5 U/mg at 14.6 h (FIG. 5).

Polymer purification from samples for molecular weight analysis proceeded as follows. Cells were pelleted by centrifugation and washed with distilled water. Cells were collected by centrifugation, lyophilized, and refluxed in chloroform for 5 h. The cellular debris was removed from the polymer solution by filtration through a sintered glass funnel. PHB was precipitated from the chloroform solution with one volume of hexane, isolated by filtration through a sintered glass funnel, and dried overnight in vacuo. $^1$H NMR analysis of the polymer dissolved in CDCl$_3$ confirmed that the isolated material was PHB in high purity [$^1$H NMR (CDCl$_3$; 300 MHz) ó=1.24(d, ξ=6.3Hz, 3H), 244 (dd, ξ=6.5, 15.5 Hz, 1H), 2.58 (dd, ξ=–7.4, 15.5, 1 H), 5.23 (m, 1H)].

Gel permeation chromatography without light scattering (FIGS. 6B and 6C) was performed on a Progel-TSK G7000H$_{XL}$ column in series with a Shodex K-805 GPC column. Polymer samples were eluted in chloroform at 1 mL/min at 30 °C.

The weight average molecular weight ($M_w$) and Polydispersity index (PDI), equivalent to $M_w/M_n$ where $M_n$ is the number average molecular weight, were measured for each polymer sample by multi-angle light scattering. Light scattering was performed using a Waters model 501 pump and model 410 differential refractometer equipped with a Shodex K-807LC GPC column and a Dawn-F multi-angle laser photometer (Wyatt Technology). Polymer samples were eluted with 2,2,2-trifluoroethanol at 35° C. Polymethyl-methacrylate standards were used to normalize the instrument and light scattering analysis of the standards yielded molecular weight values in good agreement with those reported by the supplier.

Polymer samples isolated at various time points from the fermentation of DH5α/pAeT41 possessed $M_w$ ranging from 4.3×10$^6$ to 4.0×10$^6$ Da with the exception of a small drop to 3.1×10$^6$ Da at the 23 h time point (FIG. 3B), $M_w$ values that are significantly larger than the 1.0×10$^6$ to 1.2×10$^6$ Da $M_w$ observed for polyester isolated from routine fermentations of *A. eutrophus* (Kawaguchi and Doi, *Macromolecules* 1992, 25, 2324–2329.; Hahn et al., *Biotechnology and Bioengineering*, 1994, 44, 256–261). The polydispersity index ranged from 1.01 to 1.08 during the fermentation, (FIG. 6) signifying a polymer product with a much narrow molecular weight distribution than the polymer possessing a PDI of 2.0 isolated from *A. eutrophus* by Kawaguchi and Doi (1992).

EXAMPLE 2

Increasing PHA synthase activity and effect on PHB mw.

Figure 7A:
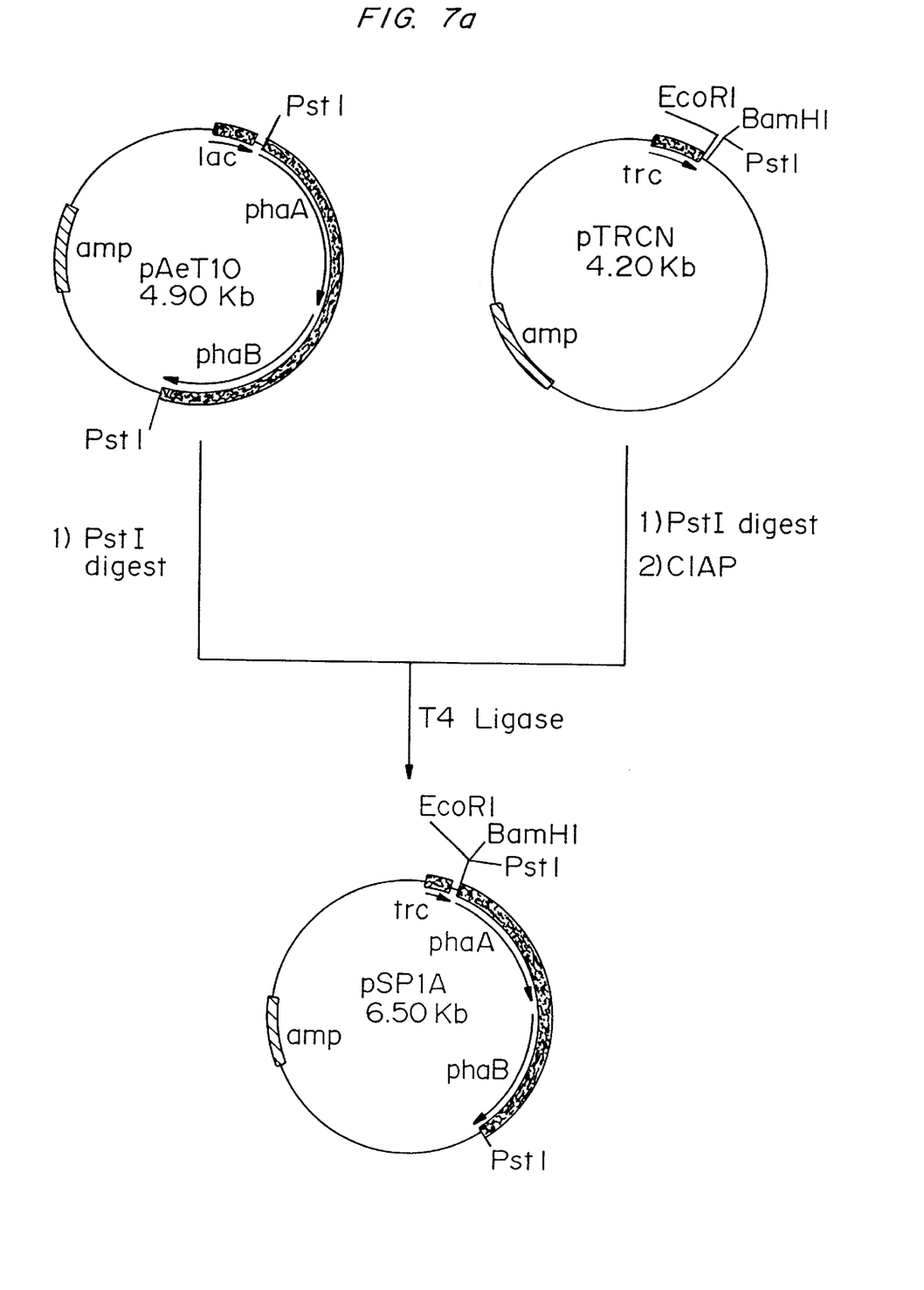
FIGS. 7A and 7B are schematics of the construction of plasmid pSP2.
Figure 7B:
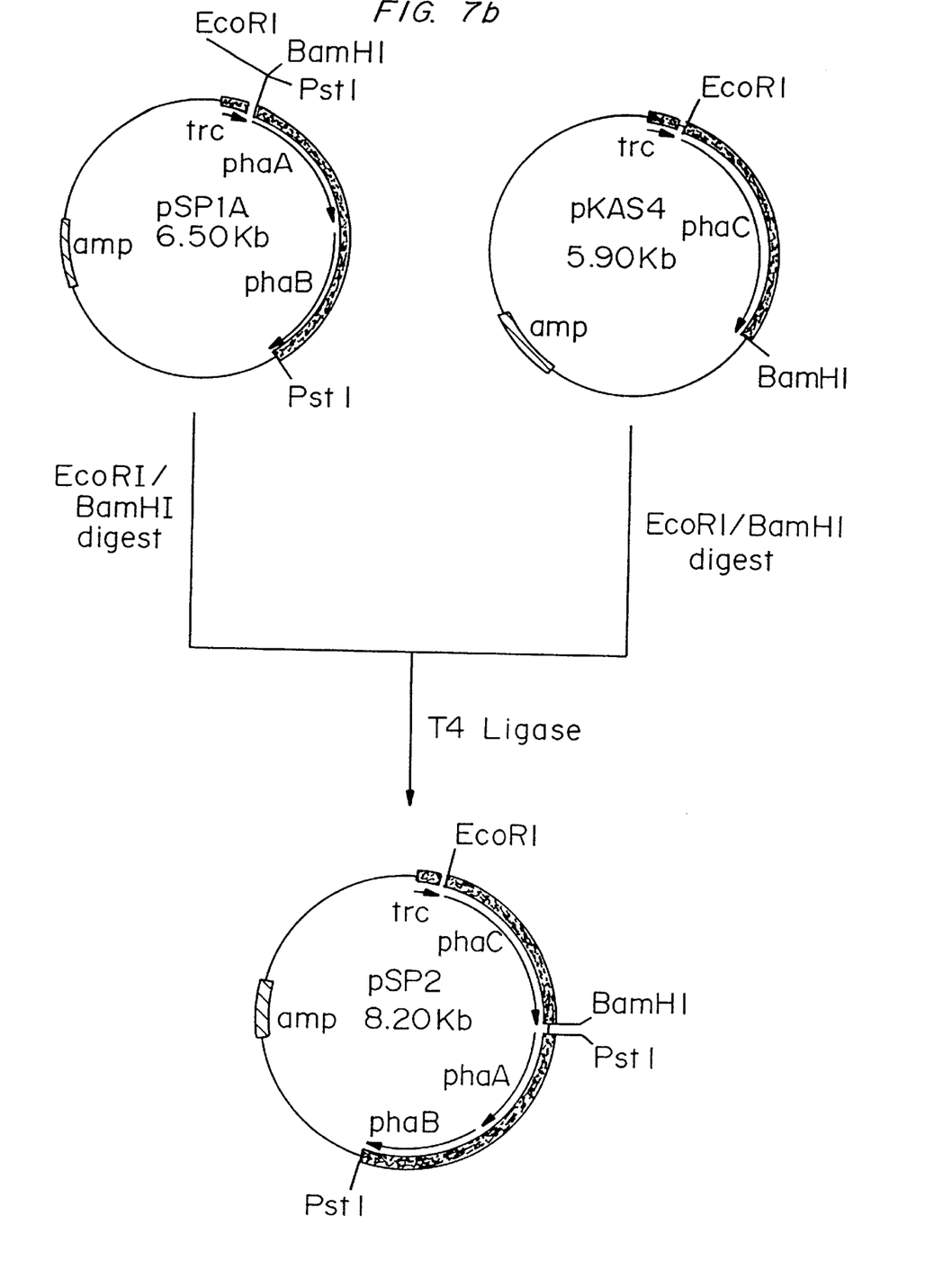

Since little or no PHA synthase activity is detected in either the soluble or insoluble fractions of DH5α/pAeT41 lysates, a new construct was designed to test the effect of elevated synthase activity on the molecular weight of PHB. An *E. coli* ribosome binding site was inserted into the plasmid in place of the *A. eutrophus* synthase ribosome binding site to increase synthase activity in the presence of genes encoding β-ketothiolase and acetoacetylCoA reductase. Plasmid pSP2 was constructed containing the strong inducible trc promoter, a gene encoding PHA synthase with an optimal *E. coli* ribosome binding site, and genes encoding the thiolase and reductase. A 2.3 kb fragment encoding β-ketothiolase (PhaA) and acetoacetyl-CoA reductase (PhaB) was isolated from plasmid pAeT10 (Peoples and Sinskey, 1989b) upon digestion with Pst I (FIGS. 7A–B). The fragment was ligated into the 4.2 kb vector pTRCN (Gerngross et al., 1994) that has been previously digested with Pst I and calf intestinal alkaline phosphatase. A plasmid containing phaA adjacent to the trc promoter of plasmid pTRCN was isolated and named pSP1A. A 1.7 kb fragment encoding PHA synthase (PhaC) was isolated from plasmid pKAS4 (Gerngross et al., 1994) upon digesting the plasmid with EcoR I and BamH I. The fragment was ligated into pSP1A that had been previously digested with EcoR I and BamH I. A 8.2 kb plasmid containing phaC behind the trc promoter, followed by a fragment containing phaA and phaB, was isolated and named pSP2 (FIG. 7B). The presence of a plasmid-borne lacI$^q$ gene on pSP2 allows the transcription of all three PHA biosynthetic genes in this synthetic operon to be tightly controlled by the amount of IPTG added to the culture medium.

Figure 1B:
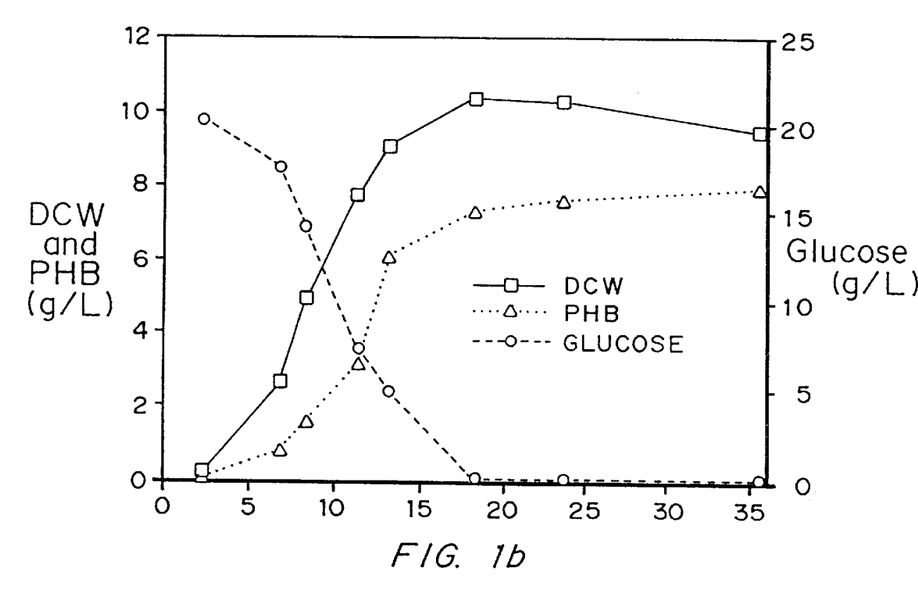
Figure 3B:
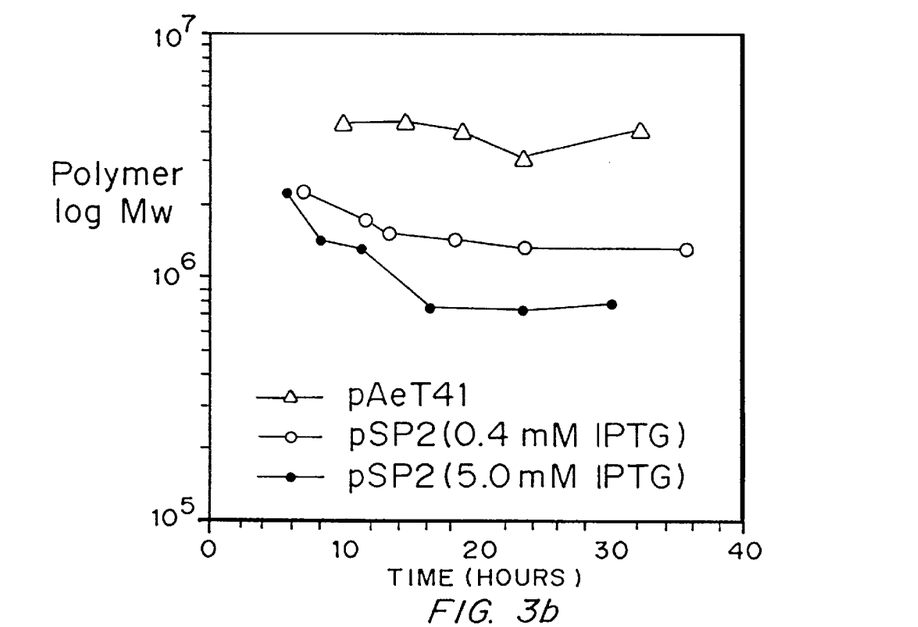
FIG. 3B is a graph illustrating multi-angle light scattering molecular weight analysis of polymer isolated from strains DH5α/pAeT41 (triangle), DH5α/pSP2 with 0.4 mM IPTG induction (circles), and DH5α/pSP2 with 5 mM IPTG induction (solid circles).

Initial batch fermentation of DH5α/pSP2 was performed in the presence of 0.4 mM IPTG which was added to the culture once the absorbance at 600 nm reached 0.6. DH5α/pSP2 induced in this manner consumed all glucose after 18.3 h of fermentation (FIG. 1B). Dry cell weight and PHB content were found to be 10.4 and 7.9 g/L at 18.3 and 35.5 h, respectively. A $M_w$ of 2.2×10$^6$ Da was detected after 6.9 h of fermentation and $M_w$ values steadily decreased until 35.5 h at which time isolated polymer possessed a $M_w$ of 1.3×10$^6$, three fold smaller than the 4.0×10$^6$ Da observed at the end of the DH5α/pAeT41 fermentation (FIG. 3B). The observed increase in PHB concentration (FIG. 1B) during the time span that a decrease in polymer molecular weight was observed (FIG. 3B) indicates that the decrease in polymer molecular weight is not due to polymer degradation during the fermentation. Enzyme activities were therefore assayed for the DH5α/pSP2 (0.4 mM IPTG) fermentation to determine if a difference in enzyme activities coincided with the observed differences in Mof polymer isolated from strains DH5α/pAeT41 and DH5α/pSP2 (0.4 mM IPTG). The most prominent difference in enzyme activity was the presence of detectable synthase activity in DH5α/pSP2 (0.4 mM IPTG), which was predominantly insoluble during the fermentation, yielding a maximum specific activity of 1.4 U/mg in the combined soluble and insoluble fractions at 13.3 h (FIG. 3A). This observation indicated that the concentration of synthase might play a role in determining the size of the polymer produced in the host cell. Soluble synthase in DH5α/pSP2 yielded a maximum activity of 0.11 U/mg at 18.3 h (FIG. 2). No reductase activity was detected in the fermentation (FIG. 4) and assays for thiolase activity yielded a maximum of 3.6 U/mg at 11.5 h time point of the fermentation (FIG. 5). The polymer isolated from the DH5α/pSP2 (0.4 mM IPTG) fermentation possessed a broader molecular weight distribution than polymer isolated from DH5α/pAeT41 as seen from the increase in polydispersity index values which reached a maximum of 1.57 (FIG. 6).

To further demonstrate the ability of PHA synthase to regulate the size of PHA produced in a host cell, the transcription of PHA biosynthetic genes in DH5α/pSP2 was elevated by increasing the concentration of the inducing agent, IPTG, to 5 mM. Maximum soluble synthase activity increased from the 0.11 U/mg observed in DH5α/pSP2 induced with 0.4 mM IPTG to 0.21 U/mg when induced with 5 mM IPTG (FIG. 2). Likewise, insoluble synthase activity increased, yielding 2.5 U/mg at 16.5 h (FIG. 3A). A further reduction of size in the isolated polymer was observed, yielding $M_w$ values of 2.2×10$^6$ Da after 5.8 h of fermentation which decreased to 7.8×10$^5$ Da at 30.2 h, a value five fold smaller than the 4.0×10$^6$ Da observed at the end of the DH5×/pAeT41 fermentation (FIG. 3B).

Figure 1C:
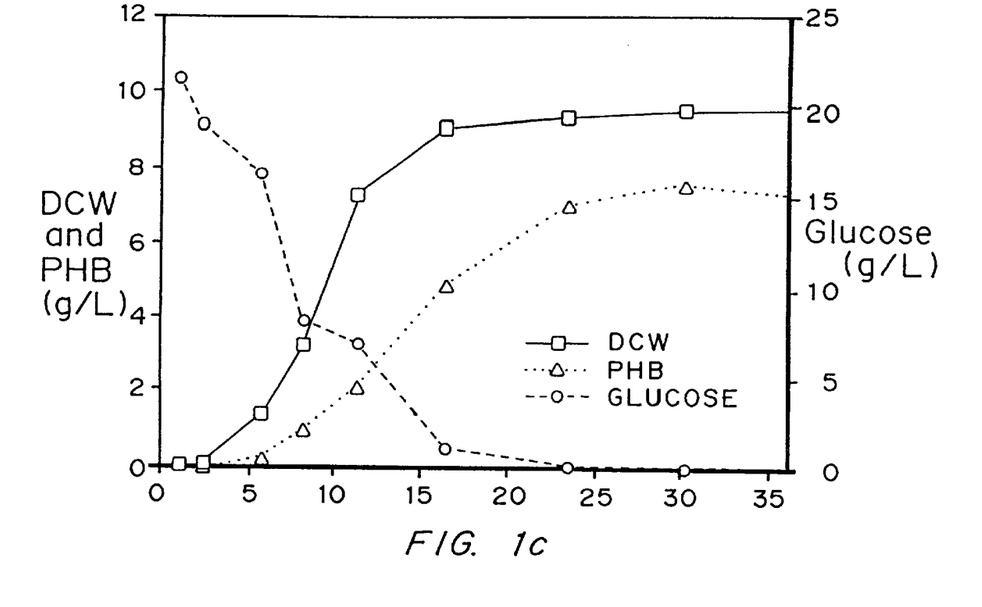

No reductase activity was detected during the fermentation (FIG. 4) and thiolase activity yielded a maximum activity of 12.3 U/mg at 16.5 h (FIG. 5). Fermentation parameters were comparable to those measured for DH560/pSP2 induced with 0.4 mM IPTG with dry cell weight and PHB concentration maximum yields of 9.5 and 7.6 g/L, respectively, at 30.2 h (FIG. 1C). All glucose was consumed from the fermentation at 16.5 h.

EXAMPLE 3

Effect of synthase activity on molecular weight distribution.

Figure 6A:
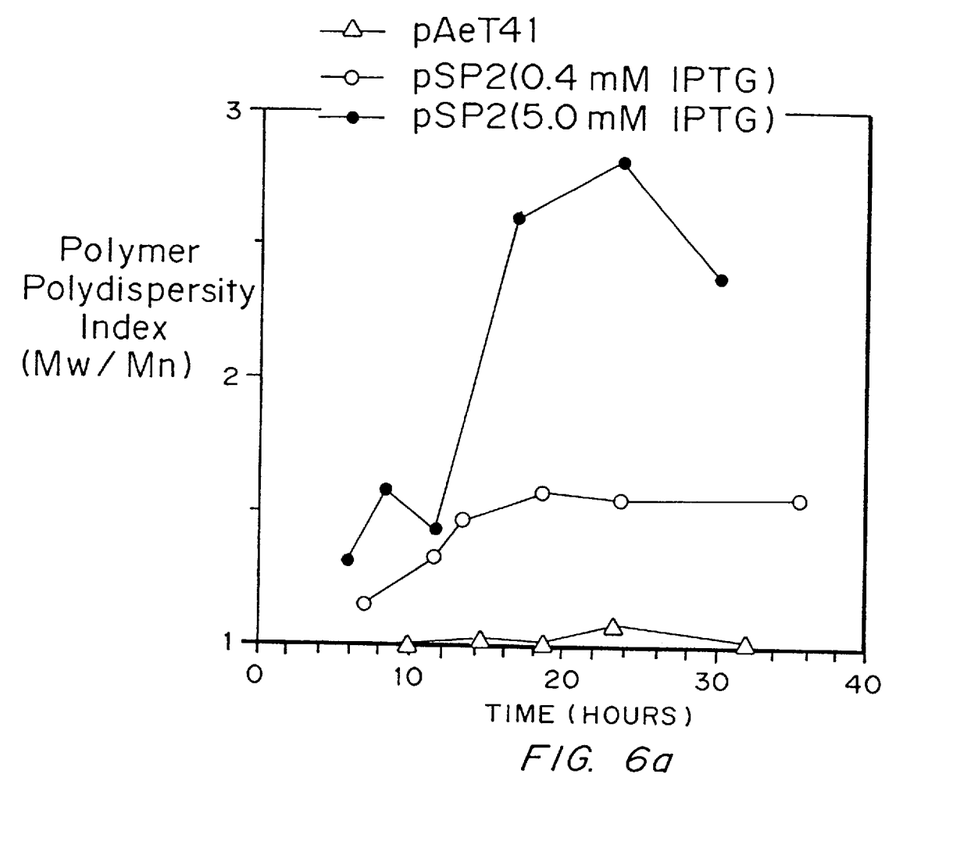
Figure 6B:
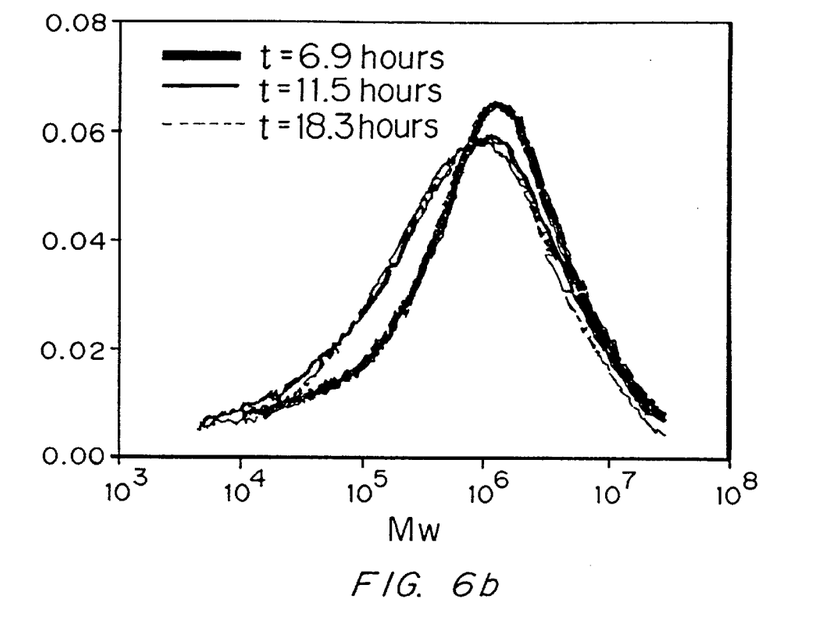
FIGS. 6B and 6C are raw gel permeation chromatograms performed without light scattering of polymer isolated from strain DH5α/pSP2 induced with 0.4 mM IPTG (FIG. 6B) and polymer isolated from strain DH5α/pSP2 induced with 5 mM IPTG (FIG. 6C).

Analysis of the results in Example 1 by GPC in line with light-scattering showed that the polydispersity index of polymer isolated from DH5α/pSP2 induced with 5 mM IPTG was 2.8 at 25.4 h, indicating a broader molecular weight distribution than polymer samples isolated from DH5α/pAeT41 and DH5α/pSP2 induced with 0.4 mM IPTG (FIG. 6A).

Figure 6C:
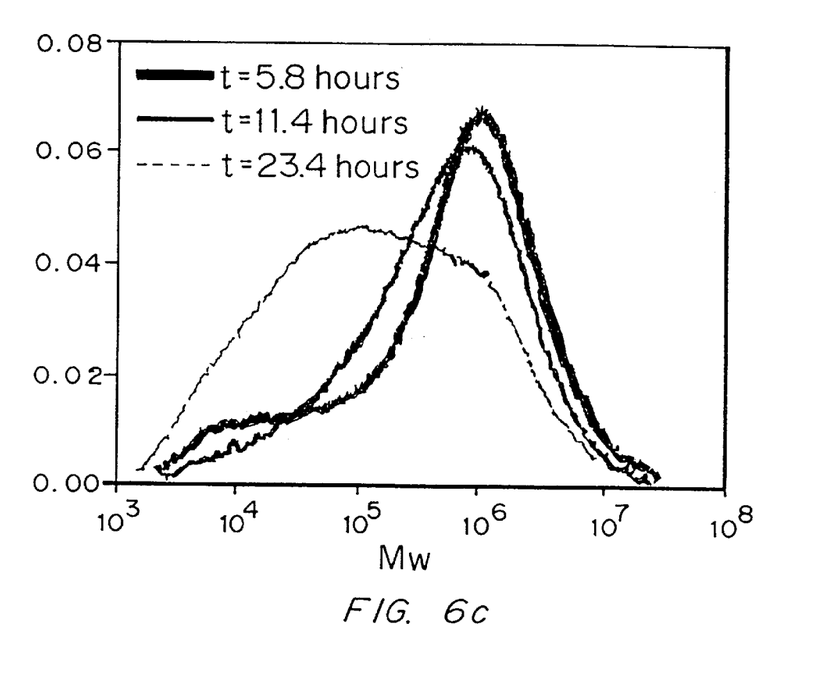

The control of molecular weight distribution is reflected by the different polydispersity indices measured for polymer samples isolated from strains DH5α/pAeT41, DH5α/pSP2 induced with 0.4 mM IPTG, and DH5α/pSP2 induced with 5 mM IPTG (FIG. 6A). The broadening of distributions upon induction of DH5α/pSP2 with IPTG can be attributed to increasing the concentration of PHA synthase midway through the fermentation. The basal levels of synthase activity before IPTG induction, due to incomplete repression of the trc promoter by the lacI$^q$ gene product, produce a small pool of polymers with high molecular weights. Induction with IPTG midway through the fermentation increases the number of polymer chains competing for substrate producing a new pool of polymers with a shorter chain length. Since the polymer pool now encompasses long chains manufactured before IPTG induction and new shorter chains produced after IPTG induction, the molecular weight distribution of the final polymer product broadens. The extent of synthase induction midway through the fermentation determines the final distribution of the polymer product. This is most evident upon examination of the GPC chromatograms of DH5α/pSP2 induced with 0.4 mM IPTG (FIG. 6B) and DH5α/pSP2 induced with 5 mM IPTG (FIG. 6C). The chromatograms of both strains reveal the production of a polymer whose median molecular weight exceeds $10^6$ Da at an early time point of the fermentation (DH5α/pSP2, 0.4 mM IPTG, 6.9 h; DH5α/pSP2, 5 mM IPTG, 5.8 h). However, upon induction of DH5α/pSP2 with either 0.4 mM or 5 mM IPTG midway through the fermentation, the median molecular weight of polymer isolated from DH5α/pSP2 induced with 5 mM IPTG (23.4 h) shifts to a lower value than polymer isolated from DH5α/pSP2 induced with 0.4 mM IPTG (18.3 h) yielding a broader molecular weight distribution for the 5 mM sample. Accordingly, varying the extent and time of induction of PHA synthase in a genetic recombinant production strain can be used to produce polymer products with different molecular weight distributions.

Modifications and variations of the present invention will be obvious from the foregoing detailed description and are intended to come within the scope of the appended claims.

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 4984 base pairs
        ( B ) TYPE: nucleic acid
        ( C ) STRANDEDNESS: double
        ( D ) TOPOLOGY: linear     ( i i ) MOLECULE TYPE: DNA     ( x i ) SEQUENCE DESCRIPTION: SEQ ID NO:1:

```
CCCGGGCAAG  TACCTTGCCG  ACATCTATGC  GCTGGCGCGC  ACGCGCCTGG  CGCGCGCCGG      60

CTGTACCGAG  GTCTACGGCG  GCGACGCCTG  CACCGTGGCC  GACGCCGGTC  GCTTCTACTC     120

CTATCGGCGC  GATGGCGTGA  CCGGCCGCAT  GGCCAGCCTG  GTCTGGCTGG  CGGACTGAGC     180

CCGCCGCTGC  CTCACTCGTC  CTTGCCCCTG  GCCGCCTGCG  CGCGCTCGGC  TTCAGCCTTG     240

CGTCGGCGGC  GGCCGGGCGT  GCCCATGATG  TAGAGCACCA  CGCCACCGGC  GCCATGCCAT     300

ACATCAGGAA  GGTGGCAACG  CCTGCCACCA  CGTTGTGCTC  GGTGATCGCC  ATCATCAGCG     360

CCACGTAGAG  CCAGCCAATG  GCCACGATGT  ACATCAAAAA  TTCATCCTTC  TCGCCTATGC     420

TCTGGGGCCT  CGGCAGATGC  GAGCGCTGCA  TACCGTCCGG  TAGGTCGGGA  AGCGTGCAGT     480

GCCGAGGCGG  ATTCCCGCAT  TGACAGCGCG  TGCGTTGCAA  GGCAACAATG  GACTCAAATG     540

TCTCGGAATC  GCTGACGATT  CCCAGGTTTC  TCCGGCAAGC  ATAGCGCATG  GCGTCTCCAT     600

GCGAGAATGT  CGCGCTTGCC  GGATAAAAGG  GGAGCCGCTA  TCGGAATGGA  CGCAAGCCAC     660

GGCCGCAGCA  GGTGCGGTCG  AGGGCTTCCA  GCCAGTTCCA  GGGCAGATGT  GCCGGCAGAC     720

CCTCCCGCTT  TGGGGGAGGC  GCAAGCCGGG  TCCATTCGGA  TAGCATCTCC  CCATGCAAAG     780

TGCCGGCCAG  GGCAATGCCC  GGAGCCGGTT  CGAATAGTGA  CGGCAGAGAG  ACAATCAAAT     840

CATGGCGACC  GGCAAAGGCG  CGGCAGCTTC  CACGCAGGAA  GGCAAGTCCC  AACCATTCAA     900
```

| | | | | | |
|---|---|---|---|---|---|
| GGTCACGCCG | GGGCCATTCG | ATCCAGCCAC | ATGGCTGGAA | TGGTCCCGCC | AGTGGCAGGG | 960 |
| CACTGAAGGC | AACGGCCACG | CGGCCGCGTC | CGGCATTCCG | GGCCTGGATG | CGCTGGCAGG | 1020 |
| CGTCAAGATC | GCGCCGGCGC | AGCTGGGTGA | TATCCAGCAG | CGCTACATGA | AGGACTTCTC | 1080 |
| AGCGCTGTGG | CAGGCCATGG | CCGAGGGCAA | GGCCGAGGCC | ACCGGTCCGC | TGCACGACCG | 1140 |
| GCGCTTCGCC | GGCGACGCAT | GGCGCACCAA | CCTCCCATAT | CGCTTCGCTG | CCGCGTTCTA | 1200 |
| CCTGCTCAAT | GCGCGCGCCT | TGACCGAGCT | GGCCGATGCC | GTCGAGGCCG | ATGCCAAGAC | 1260 |
| CCGCCAGCGC | ATCCGCTTCG | CGATCTCGCA | ATGGGTCGAT | GCGATGTCGC | CCGCCAACTT | 1320 |
| CCTTGCCACC | AATCCCGAGG | CGCAGCGCCT | GCTGATCGAG | TCGGGCGGCG | AATCGCTGCG | 1380 |
| TGCCGGCGTG | CGCAACATGA | TGGAAGACCT | GACACGCGGC | AAGATCTCGC | AGACCGACGA | 1440 |
| GAGCGCGTTT | GAGGTCGGCC | GCAATGTCGC | GGTGACCGAA | GGCGCCGTGG | TCTTCGAGAA | 1500 |
| CGAGTACTTC | CAGCTGTTGC | AGTACAAGCC | GCTGACCGAC | AAGGTGCACG | CGCGCCCGCT | 1560 |
| GCTGATGGTG | CCGCCGTGCA | TCAACAAGTA | CTACATCCTG | GACCTGCAGC | CGGAGAGCTC | 1620 |
| GCTGGTGCGC | CATGTGGTGG | AGCAGGGACA | TACGGTGTTT | CTGGTGTCGT | GGCGCAATCC | 1680 |
| GGACGCCAGC | ATGGCCGGCA | GCACCTGGGA | CGACTACATC | GAGCACGCGG | CCATCCGCGC | 1740 |
| CATCGAAGTC | GCGCGCGACA | TCAGCGGCCA | GGACAAGATC | AACGTGCTCG | GCTTCTGCGT | 1800 |
| GGGCGGCACC | ATTGTCTCGA | CCGCGCTGGC | GGTGCTGGCC | GCGCGCGGCG | AGCACCCGGC | 1860 |
| CGCCAGCGTC | ACGCTGCTGA | CCACGCTGCT | GGACTTTGCC | GACACGGGCA | TCCTCGACGT | 1920 |
| CTTTGTCGAC | GAGGGCCATG | TGCAGTTGCG | CGAGGCCACG | CTGGGCGGCG | GCGCCGGCGC | 1980 |
| GCCGTGCGCG | CTGCTGCGCG | GCCTTGAGCT | GGCCAATACC | TTCTCGTTCT | TGCGCCCGAA | 2040 |
| CGACCTGGTG | TGGAACTACG | TGGTCGACAA | CTACCTGAAG | GGCAACACGC | CGGTGCCGTT | 2100 |
| CGACCTGCTG | TTCTGGAACG | GCGACGCCAC | CAACCTGCCG | GGGCCGTGGT | ACTGCTGGTA | 2160 |
| CCTGCGCCAC | ACCTACCTGC | AGAACGAGCT | CAAGGTACCG | GGCAAGCTGA | CCGTGTGCGG | 2220 |
| CGTGCCGGTG | GACCTGGCCA | GCATCGACGT | GCCGACCTAT | ATCTACGGCT | CGCGCGAAGA | 2280 |
| CCATATCGTG | CCGTGGACCG | CGGCCTATGC | CTCGACCGCG | CTGCTGGCGA | ACAAGCTGCG | 2340 |
| CTTCGTGCTG | GGTGCGTCGG | GCCATATCGC | CGGTGTGATC | AACCCGCCGG | CCAAGAACAA | 2400 |
| GCGCAGCCAC | TGGACTAACG | ATGCGCTGCC | GGAGTCGCCG | CAGCAATGGC | TGGCCGGCGC | 2460 |
| CATCGAGCAT | CACGGCAGCT | GGTGGCCGGA | CTGGACCGCA | TGGCTGGCCG | GGCAGGCCGG | 2520 |
| CGCGAAACGC | GCCGCGCCCG | CCAACTATGG | CAATGCGCGC | TATCGCGCAA | TCGAACCCGC | 2580 |
| GCCTGGGCGA | TACGTCAAAG | CCAAGGCATG | ACGCTTGCAT | GAGTGCCGGC | GTGCGTCATG | 2640 |
| CACGGCGCCG | GCAGGCCTGC | AGGTTCCCTC | CCGTTTCCAT | TGAAAGGACT | ACACAATGAC | 2700 |
| TGACGTTGTC | ATCGTATCCG | CCGCCCGCAC | CGCGGTCGGC | AAGTTTGGCG | GCTCGCTGGC | 2760 |
| CAAGATCCCG | GCACCGGAAC | TGGGTGCCGT | GGTCATCAAG | GCCGCGCTGG | AGCGCGCCGG | 2820 |
| CGTCAAGCCG | GAGCAGGTGA | GCGAAGTCAT | CATGGGCCAG | GTGCTGACCG | CCGGTTCGGG | 2880 |
| CCAGAACCCC | GCACGCCAGG | CCGCGATCAA | GGCCGGCCTG | CCGGCGATGG | TGCCGGCCAT | 2940 |
| GACCATCAAC | AAGGTGTGCG | GCTCGGGCCT | GAAGGCCGTG | ATGCTGGCCG | CCAACGCGAT | 3000 |
| CATGGCGGGC | GACGCCGAGA | TCGTGGTGGC | CGGCGGCCAG | GAAAACATGA | GCGCCGCCCC | 3060 |
| GCACGTGCTG | CCGGGCTCGC | GCGATGGTTT | CCGCATGGGC | GATGCCAAGC | TGGTCGACAC | 3120 |
| CATGATCGTC | GACGGCCTGT | GGGACGTGTA | CAACCAGTAC | CACATGGGCA | TCACCGCCGA | 3180 |
| GAACGTGGCC | AAGGAATACG | GCATCACACG | CGAGGCGCAG | GATGAGTTCG | CCGTCGGCTC | 3240 |
| GCAGAACAAG | GCCGAAGCCG | CGCAGAAGGC | CGGCAAGTTT | GACGAAGAGA | TCGTCCCGGT | 3300 |

-continued

| | | | | | | |
|---|---|---|---|---|---|---|
| GCTGATCCCG | CAGCGCAAGG | GCGACCCGGT | GGCCTTCAAG | ACCGACGAGT | TCGTGCGCCA | 3360 |
| GGGCGCCACG | CTGGACAGCA | TGTCCGGCCT | CAAGCCCGCC | TTCGACAAGG | CCGGCACGGT | 3420 |
| GACCGCGGCC | AACGCCTCGG | GCCTGAACGA | CGGCGCCGCC | GCGGTGGTGG | TGATGTCGGC | 3480 |
| GGCCAAGGCC | AAGGAACTGG | GCCTGACCCC | GCTGGCCACG | ATCAAGAGCT | ATGCCAACGC | 3540 |
| CGGTGTCGAT | CCCAAGGTGA | TGGGCATGGG | CCCGGTGCCG | GCCTCCAAGC | GCGCCCTGTC | 3600 |
| GCGCGCCGAG | TGGACCCCGC | AAGACCTGGA | CCTGATGGAG | ATCAACGAGG | CCTTTGCCGC | 3660 |
| GCAGGCGCTG | GCGGTGCACC | AGCAGATGGG | CTGGGACACC | TCCAAGGTCA | ATGTGAACGG | 3720 |
| CGGCGCCATC | GCCATCGGCC | ACCCGATCGG | CGCGTCGGGC | TGCCGTATCC | TGGTGACGCT | 3780 |
| GCTGCACGAG | ATGAAGCGCC | GTGACGCGAA | GAAGGGCCTG | GCCTCGCTGT | GCATCGGCGG | 3840 |
| CGGCATGGGC | GTGGCGCTGG | CAGTCGAGCG | CAAATAAGGA | AGGGGTTTTC | CGGGGCCGCG | 3900 |
| CGCGGTTGGC | GCGGACCCGG | CGACGATAAC | GAAGCCAATC | AAGGAGTGGA | CATGACTCAG | 3960 |
| CGCATTGCGT | ATGTGACCGG | CGGCATGGGT | GGTATCGGAA | CCGCCATTTG | CCAGCGGCTG | 4020 |
| GCCAAGGATG | GCTTTCGTGT | GGTGGCCGGT | TGCGGCCCCA | ACTCGCCGCG | CCGCGAAAAG | 4080 |
| TGGCTGGAGC | AGCAGAAGGC | CCTGGGCTTC | GATTTCATTG | CCTCGGAAGG | CAATGTGGCT | 4140 |
| GACTGGGACT | CGACCAAGAC | CGCATTCGAC | AAGGTCAAGT | CCGAGGTCGG | CGAGGTTGAT | 4200 |
| GTGCTGATCA | ACAACGCCGG | TATCACCCGC | GACGTGGTGT | TCCGCAAGAT | GACCCGCGCC | 4260 |
| GACTGGGATG | CGGTGATCGA | CACCAACCTG | ACCTCGCTGT | TCAACGTCAC | CAAGCAGGTG | 4320 |
| ATCGACGGCA | TGGCCGACCG | TGGCTGGGGC | CGCATCGTCA | ACATCTCGTC | GGTGAACGGG | 4380 |
| CAGAAGGGCC | AGTTCGGCCA | GACCAACTAC | TCCACCGCCA | AGGCCGGCCT | GCATGGCTTC | 4440 |
| ACCATGGCAC | TGGCGCAGGA | AGTGGCGACC | AAGGGCGTGA | CCGTCAACAC | GGTCTCTCCG | 4500 |
| GGCTATATCG | CCACCGACAT | GGTCAAGGCG | ATCCGCCAGG | ACGTGCTCGA | CAAGATCGTC | 4560 |
| GCGACGATCC | CGGTCAAGCG | CCTGGGCCTG | CCGGAAGAGA | TCGCCTCGAT | CTGCGCCTGG | 4620 |
| TTGTCGTCGG | AGGAGTCCGG | TTTCTCGACC | GGCGCCGACT | TCTCGCTCAA | CGGCGGCCTG | 4680 |
| CATATGGGCT | GACCTGCCGG | CCTGGTTCAA | CCAGTCGGCA | GCCGGCGCTG | GCGCCCGCGT | 4740 |
| ATTGCGGTGC | AGCCAGCGCG | GCGCACAAGG | CGGCGGGCGT | TTCGTTTCGC | CGCCCGTTTC | 4800 |
| GCGGGCCGTC | AAGGCCCGCG | AATCGTTTCT | GCCCGCGCGG | CATTCCTCGC | TTTTTGCGCC | 4860 |
| AATTCACCGG | GTTTTCCTTA | AGCCCCGTCG | CTTTTCTTAG | TGCCTTGTTG | GGCATAGAAT | 4920 |
| CAGGGCAGCG | GCGCAGCCAG | CACCATGTTC | GTGCAGCGCG | GCCCTCGCGG | GGGCGAGGCT | 4980 |
| GCAG | | | | | | 4984 |

We claim:

1. A method for controlling the molecular weight and polydispersity of a polyhydroxyalkanoate comprising a) selecting a desired molecular weight and polydispersity of the polyhydroxyalkanoate, and b) controlling the amount of polyhydroxyalkanoate synthase activity in a host expressing the synthase and providing substrate for polymerization of the polyhydroxyalkanoate, such that the polyhydroxyalkanoate with the desired molecular weight and polydispersity is produced, wherein the molecular weight of the polyhydroxyalkanoate is inversely proportional to the polyhydroxyalkanoate synthase activity.

2. The method of claim 1 wherein the amount of synthase activity is controlled by engineering the gene encoding the synthase to be under the control of an inducible promoter and regulating the expression of the synthase by inducing the promoter.

3. The method of claim 1 wherein the synthase activity is altered over time to increase the polydispersity of the polyhydroxyalkanoate.

4. The method of claim 1 wherein the synthase activity is maintained at substantially the same specific activity over a period of time to yield a polyhydroxyalkanoate having polydispersity index of between 1.02 and 2.81.

5. The method of claim 1 wherein the polyhydroxyalkanoate has a molecular weight of between 700,000 and 4,000,000 g/mol.

6. The method of claim 1 wherein the amount of synthase activity is controlled by increasing the activity of the synthase.

* * * * *